US010342442B2

(12) United States Patent
Hattangadi et al.

(10) Patent No.: US 10,342,442 B2
(45) Date of Patent: Jul. 9, 2019

(54) DEVICES, SYSTEMS, AND METHODS FOR ASSESSING A VESSEL

(71) Applicant: Volcano Corporation, San Diego, CA (US)

(72) Inventors: Neil Hattangadi, San Diego, CA (US); Scott Huennekens, San Diego, CA (US)

(73) Assignee: VOLCANO CORPORATION, San Diego, CA (US)

( * ) Notice: Subject to any disclaimer, the term of this patent is extended or adjusted under 35 U.S.C. 154(b) by 1405 days.

(21) Appl. No.: 13/958,439

(22) Filed: Aug. 2, 2013

(65) Prior Publication Data

US 2014/0039276 A1 Feb. 6, 2014

Related U.S. Application Data

(60) Provisional application No. 61/679,673, filed on Aug. 3, 2012.

(51) Int. Cl.

| A61B 5/02 | (2006.01) |
|---|---|
| A61B 6/00 | (2006.01) |
| A61B 6/10 | (2006.01) |
| A61B 6/12 | (2006.01) |
| A61B 5/107 | (2006.01) |

(Continued)

(52) U.S. Cl.
CPC ...... *A61B 5/02755* (2013.01); *A61B 5/02007* (2013.01); *A61B 5/0215* (2013.01); *A61B 5/0275* (2013.01); *A61B 5/1075* (2013.01); *A61B 6/10* (2013.01); *A61B 6/488* (2013.01); *A61B 6/504* (2013.01); *A61B 6/507* (2013.01); *A61B 6/5217* (2013.01); *G16H 50/50* (2018.01); *A61B 6/12* (2013.01); *A61B 6/4441* (2013.01); *A61B 6/542* (2013.01); *A61M 2025/0002* (2013.01)

(58) Field of Classification Search
CPC . A61B 5/02755; A61B 5/0215; A61B 5/0275; A61B 5/1075; A61B 6/488; A61B 6/504; A61B 6/507; A61B 6/5217
USPC .......................................... 600/301
See application file for complete search history.

(56) References Cited

U.S. PATENT DOCUMENTS

| 6,396,940 B1 | 5/2002 | Carrott et al. |
|---|---|---|
| 8,394,355 B2 | 3/2013 | Rosenmeier |

(Continued)

FOREIGN PATENT DOCUMENTS

| JP | 2010246725 A | 11/2010 |
|---|---|---|
| KR | 10-2012-0050475 A | 5/2012 |

(Continued)

OTHER PUBLICATIONS

International Searching Authority/European Patent Office, "Communication—Extended European Search Report," for European Application No. 13825998.1, dated Jul. 6, 2016, 9 pages.

(Continued)

*Primary Examiner* — Gary Jackson
*Assistant Examiner* — Sebastian X Lukjan

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries utilizing external imaging.

30 Claims, 11 Drawing Sheets

(51) Int. Cl.
*A61M 25/00* (2006.01)
*G16H 50/50* (2018.01)
*A61B 5/0215* (2006.01)
*A61B 5/0275* (2006.01)

(56) References Cited

U.S. PATENT DOCUMENTS

| | | |
|---|---|---|
| 2003/0191400 A1 | 10/2003 | Shalman et al. |
| 2004/0249270 A1 | 12/2004 | Kondo et al. |
| 2004/0249570 A1 | 12/2004 | Kondo et al. |
| 2006/0159621 A1 | 7/2006 | Barrett |
| 2006/0184066 A1 | 8/2006 | Karmonik |
| 2007/0021816 A1 | 1/2007 | Rudin |
| 2007/0038061 A1* | 2/2007 | Huennekens ......... A61B 6/504 600/407 |
| 2010/0063405 A1 | 3/2010 | Kashif |
| 2010/0152570 A1* | 6/2010 | Navab ................ A61B 6/463 600/411 |
| 2010/0189337 A1* | 7/2010 | Jandt ................. A61B 6/463 382/132 |
| 2011/0085977 A1 | 4/2011 | Rosenmeier |
| 2012/0041739 A1* | 2/2012 | Taylor ............... A61B 5/02007 703/11 |
| 2013/0116739 A1* | 5/2013 | Brada ................. A61B 6/486 607/9 |

FOREIGN PATENT DOCUMENTS

| | | |
|---|---|---|
| WO | 200053081 A1 | 9/2000 |
| WO | WO 01/13779 A2 | 3/2001 |
| WO | WO 2004-075756 A1 | 9/2004 |
| WO | 2010021307 A2 | 2/2012 |
| WO | 2012155040 A1 | 11/2012 |
| WO | 2013019840 A1 | 2/2013 |

OTHER PUBLICATIONS

International Searching Authority/Munich, "Supplementary Partial European Search Report," for EP Application No. 13825998.1, dated Mar. 17, 2016, 6 pages.
International Search Report and Written Opinion received in Patent Cooperation Treaty Application No. PCT/US2013/053485, dated Nov. 25, 2013, 9 pages.
Roy, Abhijit Sinha et al "Delineating the Guide-Wire Flow Obstruction Effect in Assessment of Fractional Flow Reserve and Coronary Flow Reserve Measurements", American Journal of Physiology—Heart and Circulatory Physiology, vol. 289, Jul. 2005.

* cited by examiner

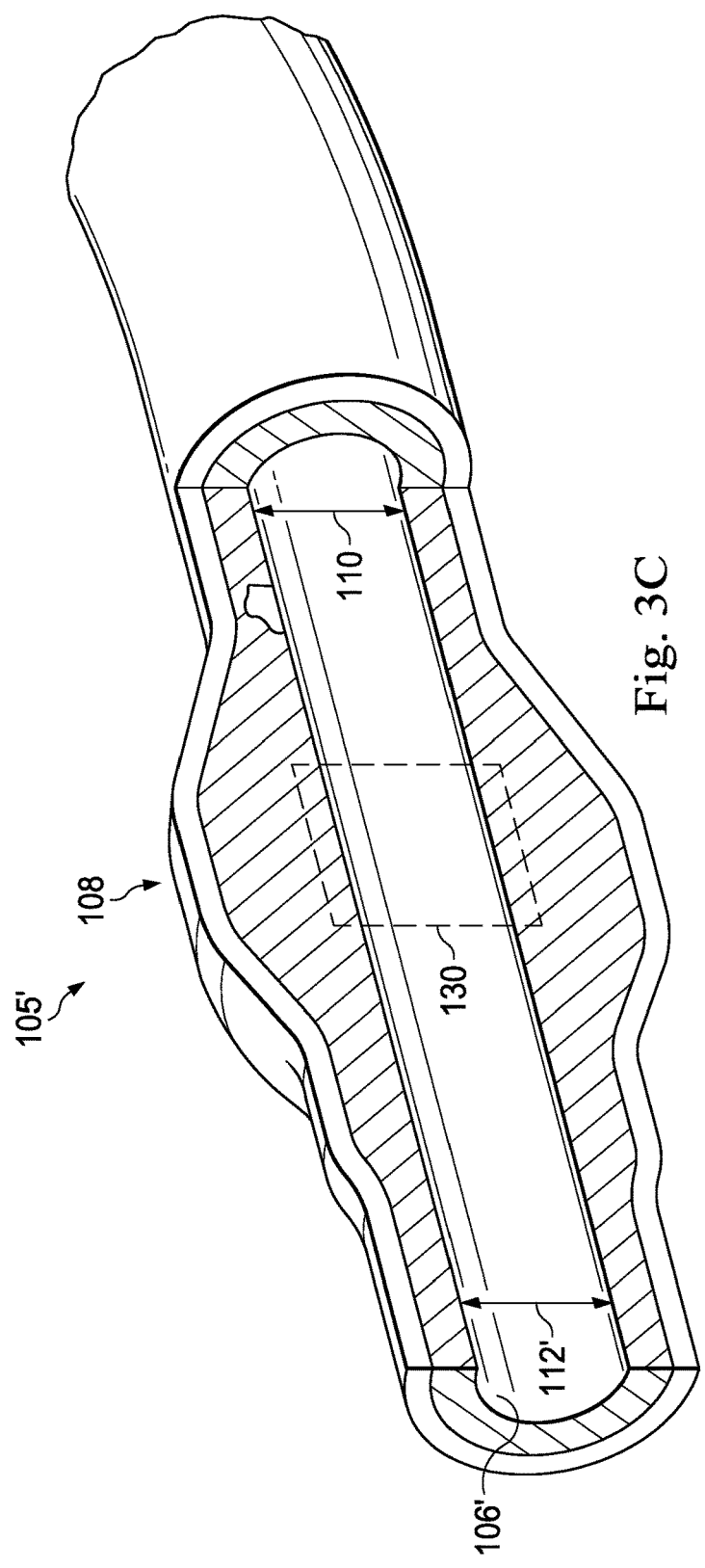

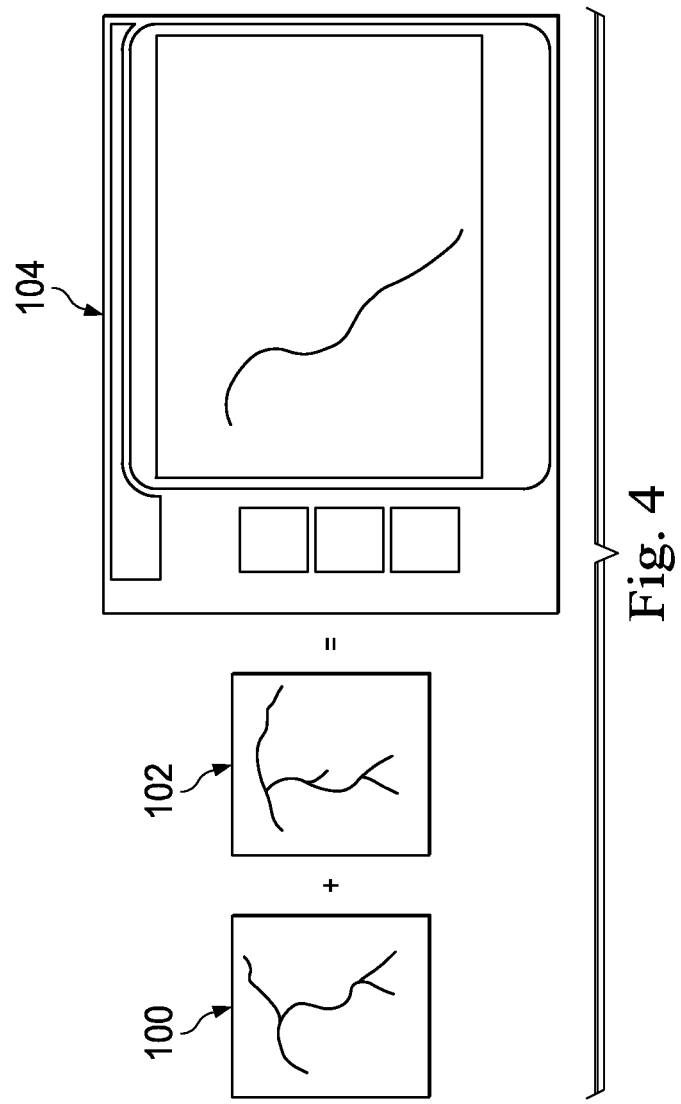

DEVICES, SYSTEMS, AND METHODS FOR ASSESSING A VESSEL

CROSS-REFERENCE TO RELATED APPLICATIONS

The present application claims priority to and the benefit of U.S. Provisional Patent Application No. 61/679,673, filed Aug. 3, 2012, which is hereby incorporated by reference herein in its entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Minimally invasive sensors may be positioned distally and proximally of the lesion of interest to detect pressures which may then be used to estimate FFR. In traditional pressure sensing FFR procedures, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

This application incorporates the following patents and applications by reference herein: U.S. Pat. Nos. 7,930,014 and 8,157,742 along with application Ser. No. 13/460,296 filed: Apr. 30, 2012, entitled: "Devices, Systems, and Methods for Assessing a Vessel;" and application Ser. No. 11/473,974 filed Jun. 23, 2006, entitled "Three Dimensional Co-Registration for Intravascular Diagnosis and Therapy;" and U.S. Provisional Patent Application No. 61/525,736 filed on Aug. 20, 2011 and U.S. Provisional Patent Application No. 61/525,739 filed on Aug. 20, 2011, each of which is hereby incorporated by reference in its entirety.

As described more fully in application Ser. No. 13/460,296 filed: Apr. 30, 2012, entitled: "Entitled: Devices, Systems, and Methods for Assessing a Vessel", incorporated by referenced herein in its entirety, new techniques have been developed to determine FFR without the use of hyperemic agents.

As recognized in U.S. Pat. No. 8,157,742 entitled "Method and System for Patient-Specific Modeling of Blood Flow," incorporated by reference herein in its entirety, coronary computed tomographic angiography (CCTA) may be used for imaging of patient with chest pain and involves using computed tomography (CT) technology to image the heart and the coronary arteries following an intra-venous infusion of contrast agent. The CT data is used to generate a 3D model of the heart and coronary arteries. This model is then used to estimate FFR.

CT scanning is a costly procedure and takes time during the critical time a patient is experiencing chest pains. Moreover, the CT machine is not located in the catheter lab where treatment can be administered.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries in a staged manner that can quickly assess severity and incorporate additional assessment modalities if more detailed information is needed to assess the patient's condition.

SUMMARY

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries.

In some instances, a method of evaluating a vessel of a patient is provided. The method includes obtaining angiographic images and determining anatomic vessel measurements from the images. In one aspect, the method includes obtaining a first set of angiographic images of the vessel having a lesion from a first view plane, collecting a first set of anatomic vessel measurements, and determining a first flow value utilizing the measurements. In one aspect, the first set of anatomic vessel measurements includes at least one first lesion diameter, a first proximal vessel diameter proximal to the lesion, and a first distal vessel diameter distal to the lesion. In one aspect, determining a first flow value includes utilizing the at least one first lesion diameter. In one aspect, the method includes creating a hypothetical vessel extending from a proximal end to a distal end, and determining a second flow value for the hypothetical vessel. In one aspect, the method includes calculating a first anatomical fractional flow reserve for the vessel by dividing the first flow value by the second flow value. In another aspect, a method for evaluating vascular flow in a current patient by utilizing a patient database of vessel flow data from a plurality of patients is provided. The method comprises obtaining angiographic images of a vessel from each of the plurality of patients, and collecting anatomic vessel measurements for the vessel from each of the plurality of patients. In one aspect, the anatomic vessel measurements include at least one proximal lesion diameter, at least one distal lesion diameter, a proximal vessel diameter proximal to the lesion, and a distal vessel diameter distal to the lesion. In one aspect, the method includes storing the anatomic vessel measurements for the vessel from each of the plurality of patients, determining an anatomical fractional flow reserve for the vessel from each of the plurality of patients, correlating the anatomical vessel measurements and the anatomical fractional flow reserve for the vessel from each of the plurality of patients, and storing the anatomical vessel measurements and the anatomical fractional flow reserve for the vessel from each of the plurality of patients as correlated data. In one aspect, the method includes associating a degree of error for each of a plurality of ranges of stored fractional flow reserves based on the correlated data. In one aspect, the method includes determining a current degree of error for a calculated fractional flow reserve for the current patient. In one aspect, the method includes determining a current degree of error for a calculated fractional flow reserve for the current patient by determining the range of stored fractional flow reserves within which the calculated fractional flow reserve lies and selecting the associated degree of error, then outputting an error corrected FFR value to a user.

In another form, a method of evaluation a vessel is provided. The method includes obtaining a plurality of angiographic images of a vessel while a contrast media of a first volume is flowing through the vessel. Determining a first vessel flow value based on the time elapsed for the first volume of contrast media to flow through the vessel. Determining a second vessel flow value based on an approximation assuming a vessel constriction is absent, and then determining a fractional flow reserve based on the determined first vessel flow value and the second vessel flow value.

In still another aspect, a method of determining a fractional flow reserve includes at least one of obtaining angiographic images and determining anatomic vessel measurements from the images and obtaining a plurality of angiographic images of a vessel while a contrast media of a first volume is flowing through the vessel. Comparing information determined from the obtaining steps to a database of prior patient information and determining, at least in part, a fractional flow reserve value based on the prior patient information.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIGS. 3A-3C are stylized cross-sectional images of vessels.

FIG. 4 is a stylized image showing creation of a three dimensional angiographic image.

DETAILED DESCRIPTION

Figure 1:
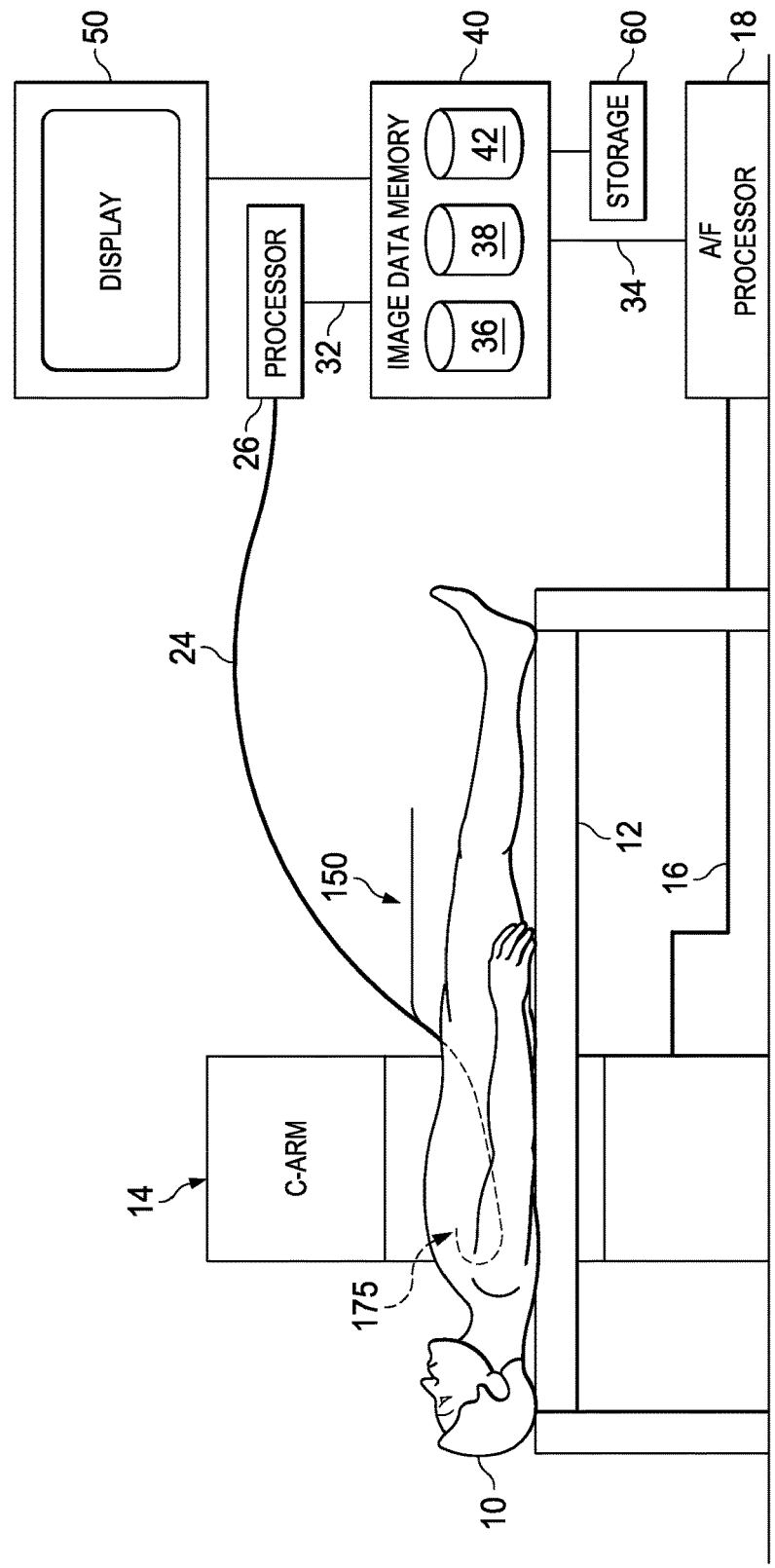
FIG. 1 is a stylized image of a patient within a catheter lab.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Turning initially to FIG. 1, an exemplary system is schematically depicted for carrying out the present invention in the form of co-registration of angiogram/fluoroscopy and if needed, intravascular functional measurement devices along with imaging diagnostic devices. The radiological, intravascular functional measurement and image data acquisition sub-systems are generally well known in the art. With regard to the radiological image data, a patient 10 is positioned upon an angiographic table 12 with at least a distal portion 175 of the catheter system 150 disposed within the patient. The angiographic table 12 is arranged to provide sufficient space for the positioning of an angiography/fluoroscopy unit c-arm 14 in an operative position in relation to the patient 10 on the table 12. Radiological image data acquired by the angiography/fluoroscopy c-arm 14 passes to an angiography/fluoroscopy processor 18 via transmission cable 16. The angiography/fluoroscopy processor 18 converts the received radiological image data received via the cable 16 into angiographic/fluoroscopic image data. The angiographic/fluoroscopic ("radiological") image data is initially stored within the processor 18.

Angiographic image data can be passed to image data memory 40 via communication line 34. Image data memory 40 may have one or more data portions 36, 38 and 42.

Additional processing of the image data including calculations of vessel anatomy, flow rates, fractional flow reserves (FFR), etc. may be performed by processor 26 utilizing data stored in memory 40. The output of processor 26 may be stored in memory 40 and/or displayed on display 50. In one aspect, catheter system 150 includes one or more sensors which provide output data along line 24. More permanents data storage 60 may include removable media and/or networked systems such as hospital DICOM storage systems.

Figure 2:
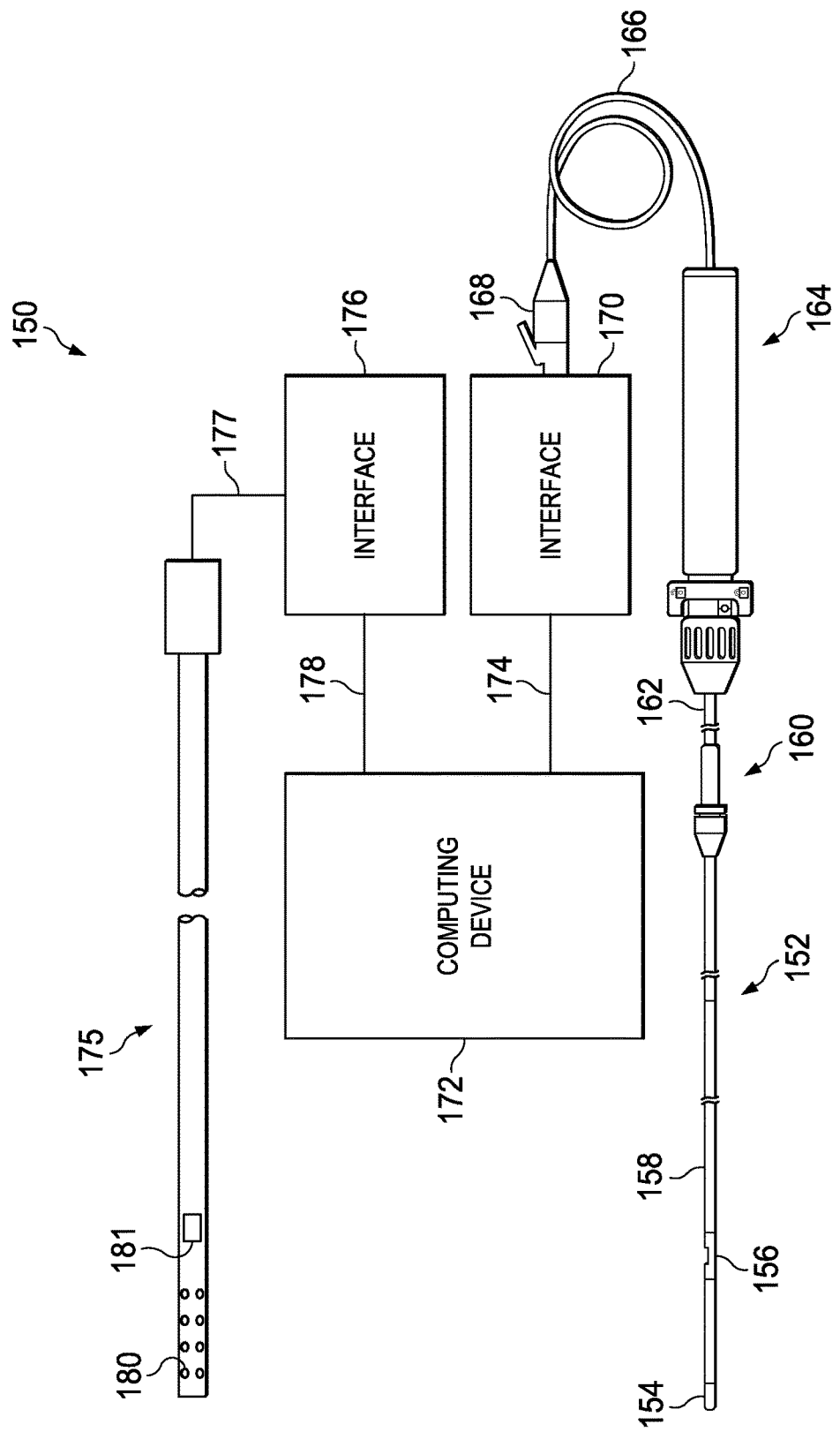
FIG. 2 is a system for performing angiographic imaging and optionally performing distal pressure sensing adjacent an obstruction within a vessel.

Referring now to FIG. 2, shown therein is a system 150 according to an embodiment of the present disclosure. In that regard, FIG. 2 is a diagrammatic, schematic view of the system 150. As shown, the system 150 includes an instrument 152. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. More specifically, processor 26 of FIG. 1 may be computing device 172. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes catheter 175 for delivery of contrast medium to the coronary arteries through perfusion holes 180. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor 181 configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

In one aspect, the catheter 175 is positioned near the coronary arteries and radiopaque contrast media is injected into the patient via holes 180. Images of the radiopaque contrast media within the coronary arteries are obtained via the angiography system.

Figure 3A:
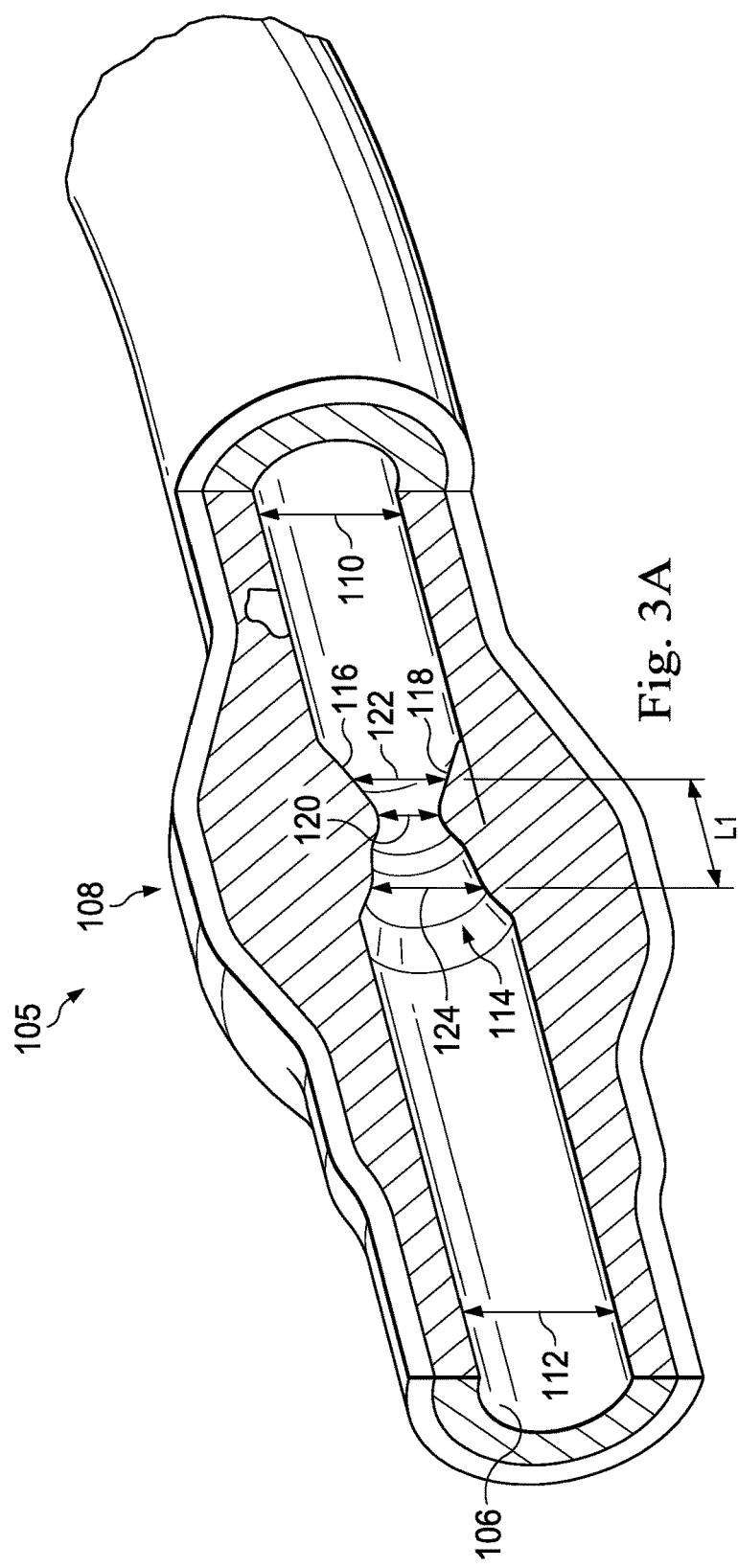
Figure 3B:
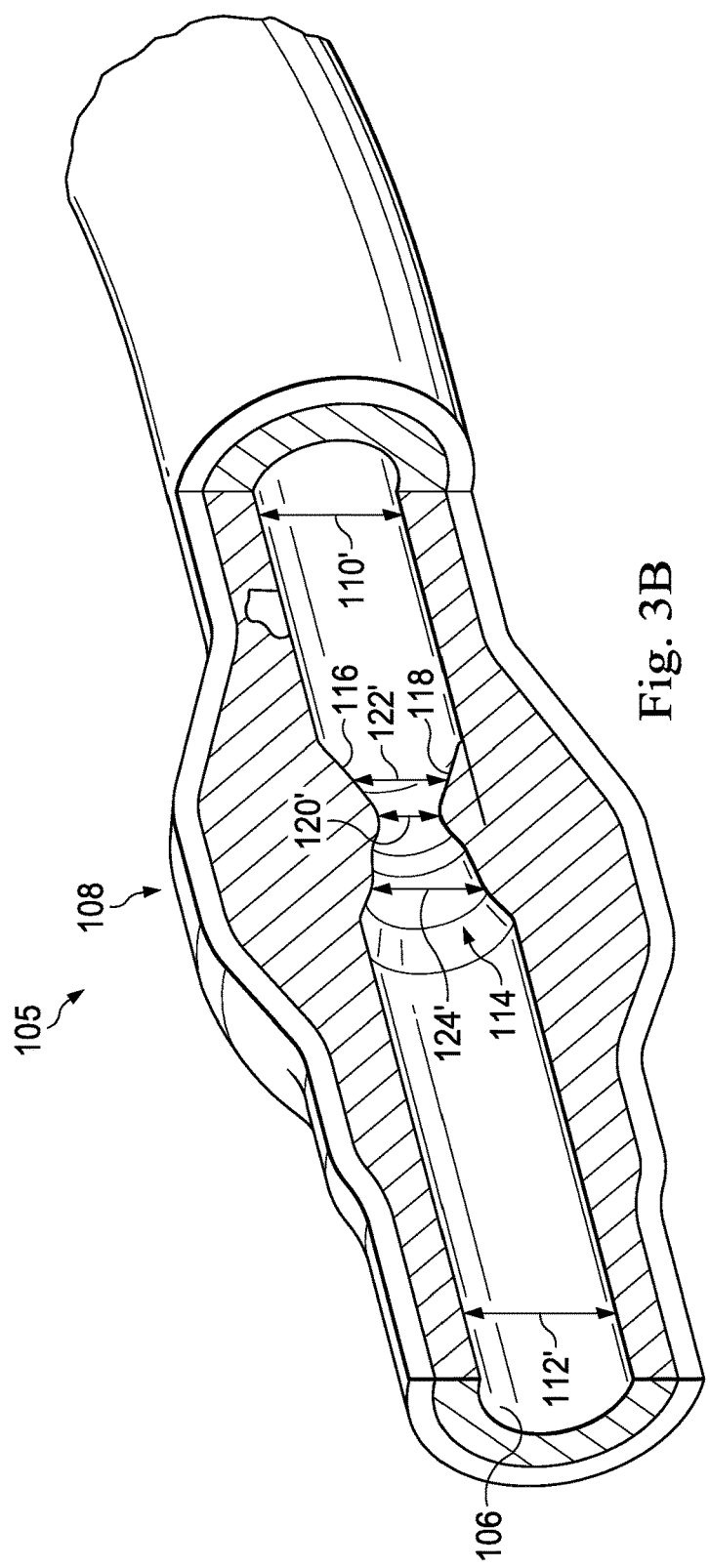

Referring now to FIGS. 3A and 3B, there are shown two stylized images of coronary vessel 105 having a stenosis 108. FIG. 3A represents the internal lumen 106 visible on angiography taken from a first view plane while FIG. 3B represents the internal lumen 106 visible on angiography taken from a second view plane rotated approximately 90 degrees with respect to the plane of FIG. 3A. Based on the angiographic image, measurements of the lumen 106 are taken proximally at point 110 to define a first proximal vessel diameter and distal of the lesion at point 112 to define a first distal diameter. A stenosis measurement is taken at the narrowest region of the vessel at point 120 to define the minimum diameter of the vessel. It is contemplated that other measurements could be taken adjacent plaque buildup 116, including taking a proximal lesion diameter measurement 122 adjacent leading portion 118 and a distal lesion diameter measurement 124 adjacent trailing portion 114. The distance L1 between diameters 122 and 124 may be determined to provide an approximation of the length of the reduced diameter region. In still a further aspect, a larger number of diameter measurements may be taken along the length of the reduced diameter region to better approximate the anatomical features of the potential lesion. The single plane measurements may be used to determine an estimate for FFR of the vessel given the single plane image data. In some embodiments, the aortic pressure measurements received from the sensor 181 may be used along with the single place measurements to determine an estimate for FFR of the vessel. However, the quality of the FFR estimation may be greatly improved by considering one or more additional vessel images taken from a different view plane. Thus, similar to the description with respect to FIG. 3A, in FIG. 3B, measurements 110', 112', 120', 122' and 124' may be taken from the angiographic image of the vessel taken in a different view plane. The measurements of FIG. 3B may be combined with the measurements of FIG. 3A to provide an improved estimate of the FFR for the vessel.

In one example, the diameter measurements of the lesion area 108 are utilized in conjunction with the sensed aortic pressure to determine a first flow value. As shown graphically in FIG. 3C, in a second portion of the estimation, a hypothetical vessel 105' is created having approximated internal lumen 106' that varies uniformly between proximal diameter 110 and distal diameter 112. Specifically, in the region 130, the reduced diameter portion has been replaced with a hypothetical lumen 106' having a smooth generally uniform diameter. Thus, the hypothetical vessel 105' is created to illustrate the baseline flow in the vessel 105 in the absence of the stenosis 108.

In some instances, the hypothetical vessel 105' is created using border detection algorithms to identify the vessel wall boundary beneath the plaque buildup 116 and craft a representation of the vessel 105 that lacks the plaque buildup 116 based on the identified vessel wall boundary. In other instances, the user may create the hypothetical vessel 105' by ignoring the plaque buildup 116 and the stenosis 108 and using point-to-point selection method to create a representative vessel having a uniformly varying luminal diameter between a point distal to the stenosis 108 and a point proximal to the stenosis 108. For example, in the pictured embodiment, the user may create the hypothetical vessel 105' by creating a representative vessel having a uniformly varying luminal diameter between the proximal diameter 110 proximal to the lesion and the distal diameter 112 distal to the lesion. In the pictured embodiment, the proximal diameter 110 and the distal diameter 112 are substantially equivalent and the hypothetical lumen 106' has a generally uniform diameter between the proximal diameter 110 and the distal diameter 112. In other embodiments where the proximal diameter 110 and the distal diameter 112 are unequal, the hypothetical lumen 106' may taper uniformly between the proximal diameter 110 and the distal diameter 112.

Accordingly, the hypothetical vessel 105' represents the vessel 105 without narrowed or stenotic areas. Based on these hypothetical dimensions, a second flow value is determined for the vessel 105. The second flow value reflects the flow rate through the vessel 105 in the absence of the lesion. In some embodiments, the second flow value is determined based on the hypothetical dimensions as well as the sensed aortic pressure. The anatomical FFR is then determined by dividing the first flow value by the second flow value. Thus, the anatomical FFR compares the flow through the vessel 105 in the presence of the lesion to the flow through the vessel 105', which represents the vessel 105 in the absence of the lesion.

FIG. 4 illustratively depicts the general concept behind a prior art three-dimensional reconstruction analysis system. A first two-dimensional angiographic image 100 taken in a first view plane and a second two-dimensional angiographic image 102, taken in a second view plane differing from the first view plane are combined and analyzed to create a graphical representation of a three-dimensional image depicted on a graphical display 104. Although only two view planes are shown for the purpose of illustration, it will be appreciated that additional view planes can be utilized to provide greater certainty in the three-dimensional representation. The image displayed on the graphical display 140 provides a much more realistic graphical representation of a lumen of an actual artery (or other blood vessel) than the typical two-dimensional angiography images.

Utilizing the three-dimensional representation and sensed aortic pressure, a first flow value can be determined for the reduced volume region. Then, as described above, the reduced volume region will be assumed to have a circumference approximating the proximal and distal vessel segments adjacent the lesion and a second flow value will be determined. The first flow value and second flow value will then be used to provide an estimate of the anatomical FFR for the three-dimensional representation of the vessel.

Either of the techniques for estimating anatomical FFR may be utilized. In at least one embodiment, both techniques are performed and then the estimated FFR values are combined for a composite anatomical FFR value. Still further, the angiographic image data may be co-registered with other sensing systems as described in U.S. Pat. No. 7,930,014 and application Ser. No. 11/473,974, each incorporated herein by reference in their entirety.

In one exemplary method of using the anatomical FFR value, if the anatomical FFR value is above or below predefined threshold values, the user may proceed to treat the patient without further diagnostic evaluation. Specifically, if anatomic FFR values are below, for example, 25%, then the patient most likely has a significant lesion requiring intervention. The user may proceed to use other diagnostic tools such as IVUS or OCT to image the lesion to determine the appropriate course of action. If the anatomic FFR values are above, for example, 90%, then the patient is not a good candidate for interventional therapy and can be treated with medications.

If the anatomical FFR values are between the example values of 25% and 90%, then additional diagnostic evaluation may be conducted to provide more detailed information into the patient's vascular condition. In one aspect the additional evaluation may include evaluating the flow through the vessel utilizing images of the contrast media flowing through the vessel.

Figure 5:
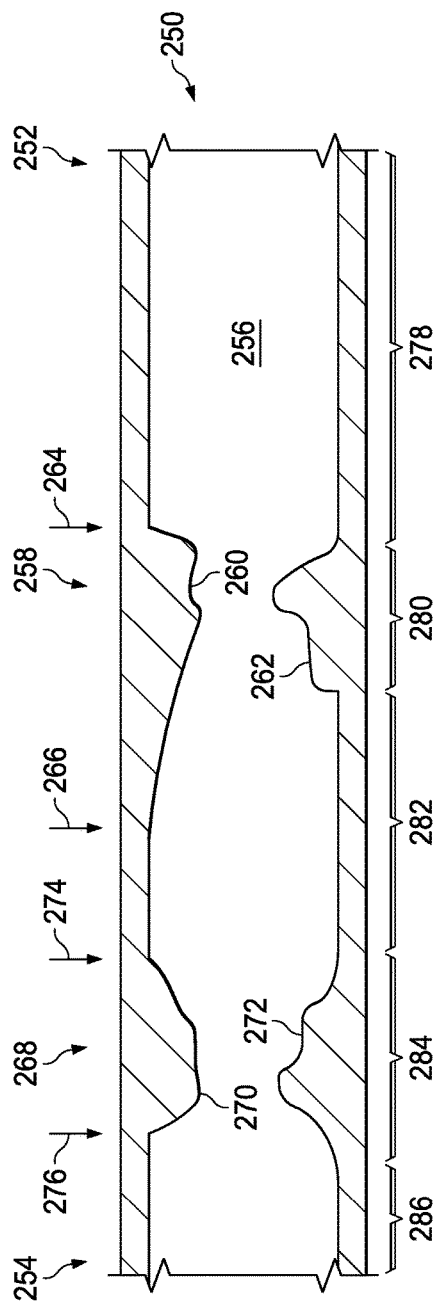
FIG. 5 is a stylized cross-sectional view of a vessel showing blockages of the lumen.

Referring more specifically to FIG. 5, shown therein is a vessel 250 according to an embodiment of the present disclosure. The vessel 250 includes a proximal portion 252 and a distal portion 254. A lumen 256 extends longitudinally along the length of the vessel 250 between the proximal portion 252 and the distal portion 254. The vessel 250 also includes a stenosis 258 having an upper portion 260 and a lower portion 262. In that regard, the upper and lower portions 260, 262 are representative of plaque buildup that narrows the lumen 256 of the vessel 250. In some instances, the plaque buildup of the stenosis 258 does not have a uniform or symmetrical profile. As shown, the stenosis 258 decreases the available space for fluid to flow through the lumen 256. In particular, the cross-sectional area of the lumen 256 is decreased by the stenosis 258. The stenosis 258 also has a proximal boundary 264 and a distal boundary 266. It should be noted that the proximal and/or distal boundaries of the upper and lower portions 260, 262 are not aligned in all instances. For example, in the illustrated embodiment the upper portion 260 tapers slowly as it extends distally, while lower portion 262 comes to a more abrupt end. In such instances, these characteristics can be taken into account when determining the boundary of the stenosis 258 as a whole. Stenosis 258 is exemplary in nature and should not be considered limiting in any way. In that regard, it is understood that the stenosis 258 has other shapes and/or compositions that limit the flow of fluid through the lumen 256 in other instances.

The vessel 250 also includes a stenosis 268 having an upper portion 270 and a lower portion 272. In that regard, the upper and lower portions 270, 272 are representative of plaque buildup that narrows the lumen 256 of the vessel 250. In some instances, the plaque buildup of the stenosis 268 does not have a uniform or symmetrical profile. As shown, the stenosis 268 decreases the available space for fluid to flow through the lumen 256. In particular, the cross-sectional area of the lumen 256 is decreased by the stenosis 268. The stenosis 268 also has a proximal boundary 274 and a distal boundary 276. It should be noted that the proximal and/or distal boundaries of the upper and lower portions 270, 272 are not aligned in all instances. Stenosis 268 is exemplary in nature and should not be considered limiting in any way. In that regard, it is understood that the stenosis 268 has other shapes and/or compositions that limit the flow of fluid through the lumen 256 in other instances.

Based on the presence of stenosis 258 and 268, the vessel 250 can be divided into five regions. Namely, region 278 located proximal of stenosis 258, region 280 located between the proximal and distal boundaries 264, 266 of stenosis 258, region 282 located between stenosis 258 and stenosis 268, region 284 located between the proximal and distal boundaries 274, 276 of stenosis 268, and region 286 located distal of stenosis 268.

Figure 6A:
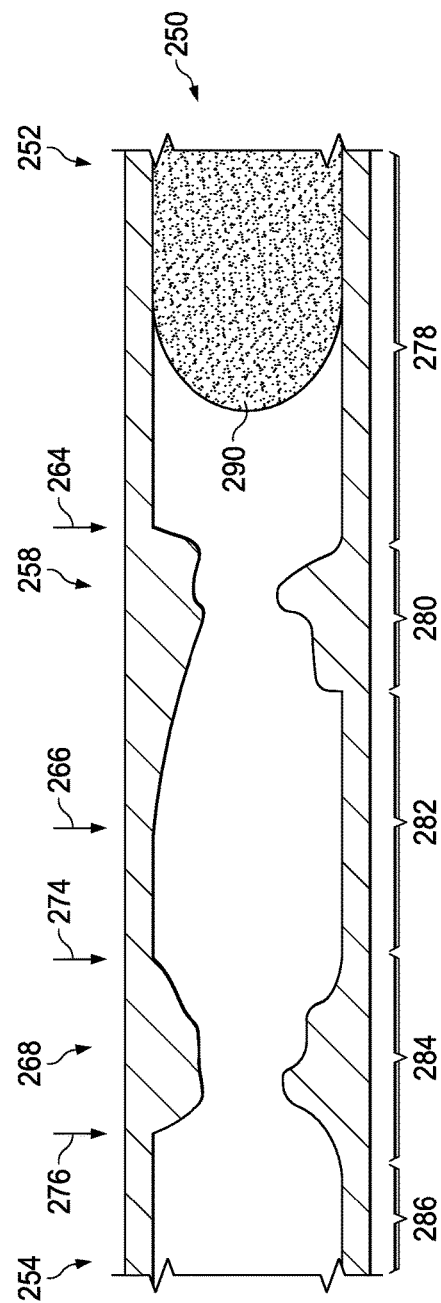
FIGS. 6A-6F illustrate the passage of a bolus of contrast media through the lumen of the vessel of FIG. 5.
Figure 6B:
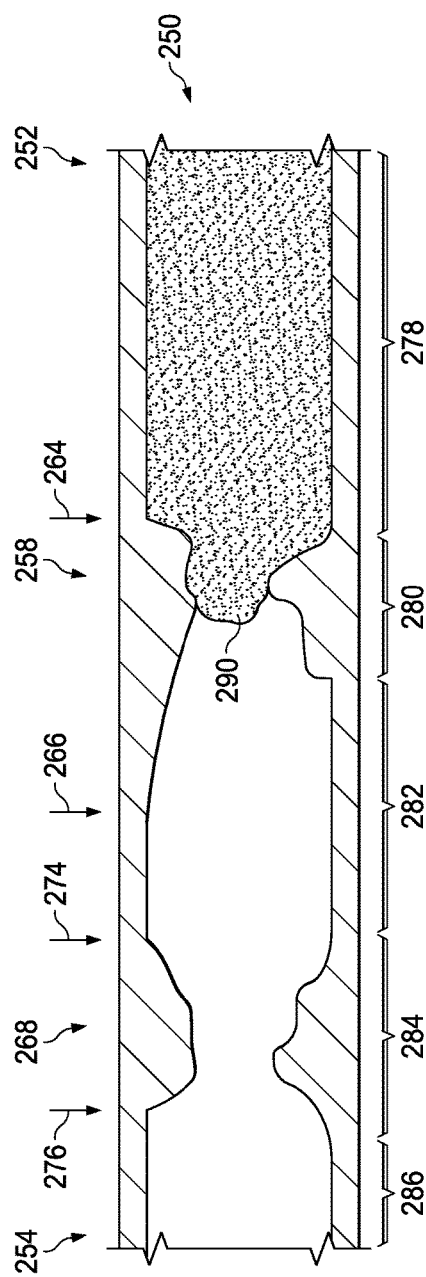
Figure 6C:
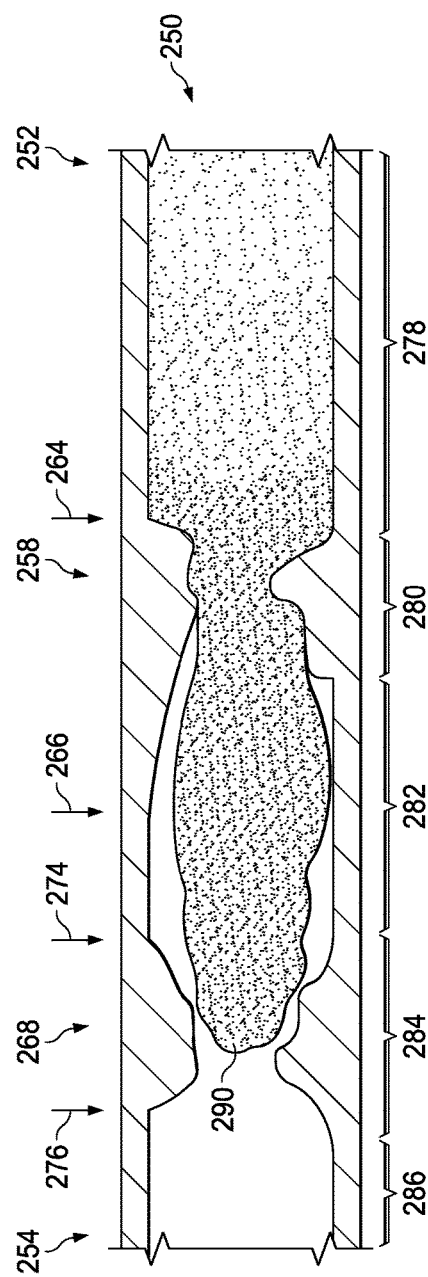
Figure 6D:
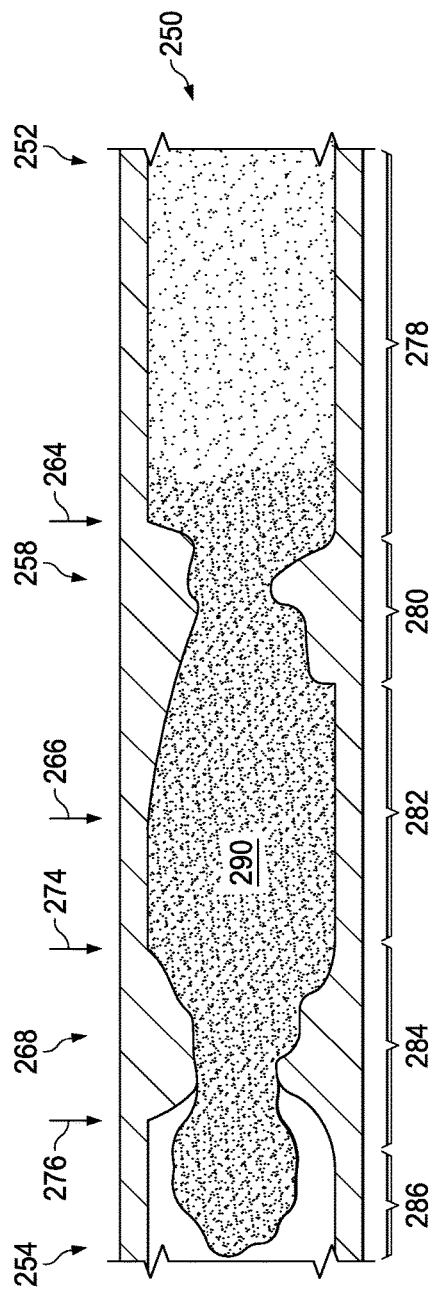
Figure 6E:
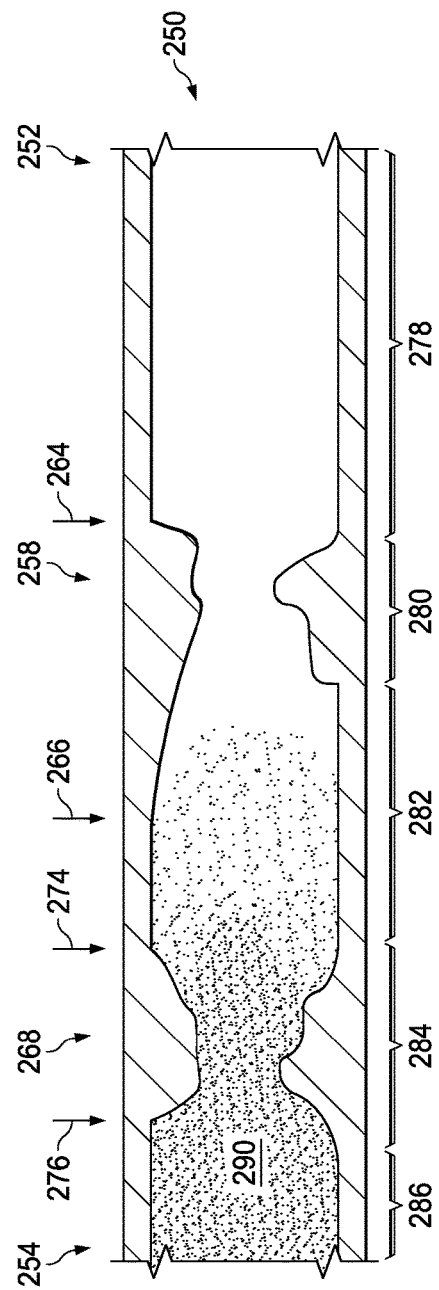
Figure 6F:
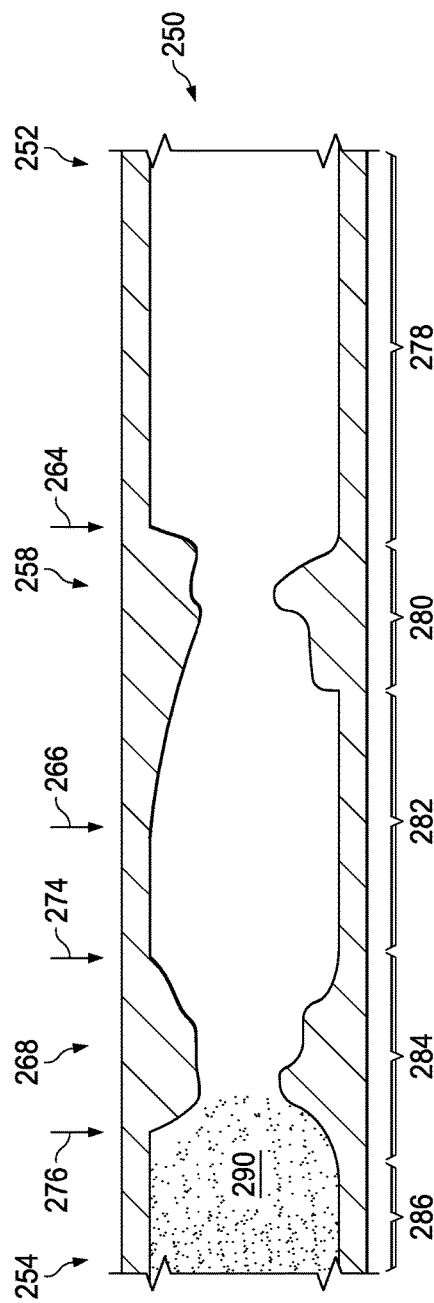

Referring now to FIGS. 6A-6F, shown therein is a series of drawings representing the flow of an angiographic contrast agent through the vessel 250. As shown, FIG. 6A shows the initial introduction of the contrast material 290 into the vessel 250. FIG. 6B shows the contrast material 290 begin to flow past stenosis 258. FIG. 6C shows the contrast material 290 reaching stenosis 268. FIG. 6D shows the contrast material 290 flowing through both stenosis 258 and stenosis 268. FIG. 6E shows contrast material 290 having completely passed stenosis 258. Finally, FIG. 6F shows the last bits of the contrast material 290 passing distally of stenosis 268.

In some implementations of the present disclosure, at least one characteristic of the flow of contrast agent through the vessel, such as, by way of non-limiting example, the color change in the angiographic images derived from the flow of the angiographic contrast agent through the vessel, is utilized to estimate a fractional flow reserve (FFR) or a flow ratio for the vessel. In this context, FFR is considered to be the flow through the vessel with the lesion or stenosis divided by the maximum flow through the vessel without the lesion or stenosis. In that regard, the estimated FFR or flow ratio is calculated across stenosis 258, across stenosis 268, and/or across both stenosis 258 and stenosis 268. Further, the color change in the angiographic images is combined with one or more of the other techniques for estimating FFR or a flow ratio in accordance with the present disclosure.

A bolus of contrast material 290 (e.g., barium, iodine, and/or gadolinium based materials) is injected into the vessel 250. In some instances, the contrast material is injected through an angiographic catheter. In that regard, a known volume of contrast material is injected into the vessel 250. In some instances, the volume of contrast material is between about 60 mL and about 80 mL, but may have larger or smaller volumes in other instances. In some implementations, a volume of contrast material is selected so that it can be flushed through the vessel with between 3 and 10 heartbeat cycles. As the contrast material 290 flows through the vessel 250, as represented in FIGS. 6A-6F, the color of the various sections of the vessel 250 will change based on the amount of contrast fluid present at a particular time. Accordingly, by tracking the change of color or pixilation of points of interest along the vessel 250 an estimated flow of the contrast material (and blood) through the vessel can be determined. For example, in some instances color changes at one or more points of interest proximal of the stenosis 258 within region 278 of the vessel are tracked. Likewise, color changes at one or both of stenosis 258 and stenosis 268 are tracked in some embodiments. In that regard, tracking color changes across a stenosis may be performed by tracking the color change at the proximal boundary of the stenosis, the distal boundary of the stenosis, intermediate points along the stenosis (e.g., midpoint, ⅓-way points, ¼-way points, etc.), and/or combinations thereof. Further still, in some instances color changes at one or more points of interest distal of stenosis 258 and proximal of stenosis 268, within region 282 of the vessel, are tracked. Finally, in some instances color changes at one or more points of interest distal of stenosis 268 within region 286 of the vessel are tracked.

In this context, a "point of interest" may be a specific point (i.e., a single pixel) on the angiographic image and/or a series of points (i.e., plurality of pixels) on the angiographic image. Where a series of points are utilized, the collective "point of interest" may be associated with a particular structural feature of the vessel (e.g., start or end of a stenosis, a specific distance from a stenosis, a portion having a desired cross-sectional size, etc.). Further, the "point of interest" may have a specified length along the vessel (e.g., 0.5 mm, 1 mm, 10 mm, etc.) in some instances. It is understood that the series of points defining the "point of interest" may have geometrical and/or non-geometrical pixel patterns. Thus, one skilled in the art will recognize that a "point of interest" may be any portion of an angiographic image where the contrast material will be depicted and any surrounding portions of the image.

In some instances, the color changes are tracked continuously, from frame-to-frame, across a pre-determined time period and/or until the contrast material has been flushed from the relevant portion of the vessel. However, in some embodiments only the angiographic frames associated with a portion of each heartbeat cycle are utilized for tracking the color changes. In that regard, in some instances only image frames associated with the diastolic portion of the heartbeat cycle are utilized. In some embodiments, a diagnostic window for each heartbeat cycle is identified using one or more of the techniques described in U.S. Provisional Patent Application No. 61/525,736 filed on Aug. 20, 2011 and/or U.S. patent application Ser. No. 13/460,296 filed on Apr. 30, 2012, each of which is hereby incorporated by reference in its entirety. Accordingly, in some embodiments, the angiographic images utilized to evaluate the vessel 250 are gate sampled based on the selected diagnostic window (i.e., those within the diagnostic window are utilized, those outside the diagnostic window are ignored or discarded).

Based on the color changes in the angiographic images associated with the contrast material passing through the vessel and/or other factors, an FFR or other flow ratio is calculated. In that regard, FFR or other flow ratio can be calculated utilizing factors such as the known volume of contrast material injected, the rate of color change at reference point(s) in the angiographic images, the total amount of time it takes the contrast material to pass through the region of interest in the vessel, vessel structure (e.g., cross-sectional area(s), length(s), etc.), sensed aortic pressure, maximum flow rate proximal of a stenosis, maximum flow rate distal of a stenosis, and/or other factors associated with the angiographic images, vessel, or both. In that regard, in some embodiments the maximum flow rate proximal of the stenosis is utilized as the basis for the denominator in an FFR or flow ratio calculation. In some instances, the maximum flow rate proximal of the stenosis is utilized as the denominator without adjustment. In other instances, the maximum flow rate proximal of the stenosis is adjusted (e.g., by taking into consideration such factors as differences in lumen size proximal and distal of a stenosis, branches extending off of the lumen of the vessel, hyperemic effects of administered drugs (including contrast materials), etc.) and the adjusted value is utilized as the denominator of the FFR or flow ratio calculation.

In some instances, one or more of the factors discussed above are utilized to best match the current vessel being evaluated to a corresponding vessel of a look-up table or database in order to estimate the FFR or flow ratio of the current vessel. In that regard, in some instances the look-up table or database is populated by empirical data created by coordinating angiograph-based data as described above with FFR or other flow ratio calculation techniques that rely on positioning intravascular devices configured to measure flow and/or pressure within the region of interest of the vessel. For example, in some instances a vessel is diagnosed using both the angiograph-based techniques described in the present disclosure as well as the flow and/or pressure measurement techniques that rely on an intravascular device having such sensing components being positioned within the vessel.

In addition to using angiographic image data to estimate FFR, the proposed disclosure contemplates utilizing distal pressure sensors mounted on guidewires or catheters. Specifically, traditional pressure measurements with such guidewire mounted pressure sensors may be taken utilizing hyperemic agents, such as adenosine, to calculate an FFR based on sensed pressure changes across the lesion. Similarly, pressure measurements can be taken without hyperemic agents to create an iFR such as disclosed in U.S. Provisional Patent Application No. 61/525,736 filed on Aug. 20, 2011 and U.S. Provisional Patent Application No. 61/525,739 filed on Aug. 20, 2011; application Ser. No. 13/460,296 Filed: Apr. 30, 2012, entitled: "Entitled: Devices, Systems, and Methods for Assessing a Vessel" each of which is hereby incorporated by reference in its entirety.

Whether using traditional FFR pressure measurements or iFR pressure measurements, the sensed pressures can be used to determine a sensed FFR value. Unfortunately, even when pressures are sensed intravascularly adjacent the lesion, there can still be uncertainty in the values leading to some uncertainty in the finally calculated sensed pressure FFR or iFR value. The sensed pressure FFR and/or iFR values can be combined with one or both of the anatomical FFR value or the flow FFR value to create a composite FFR value for the patient. The composite FFR should provide the highest degree of accuracy and provide the healthcare provide with the most accurate information concerning the fractional flow reserve of the vessel.

In a further aspect, the above anatomic data derived from angiographic images and flow data derived from the changes in flow of the contrast media may be saved to a database along with sensor data that includes pressure measurements taken by pressure sensors positioned distally of the lesion and intravascular imaging data. Such a database of empirical data may operate to calibrate for errors in algorithms for determining a fractional flow reserve. In one aspect, the database of correlated data may be utilized to determine a degree of error for the anatomic or flow-related fractional flow reserve of a current patient.

In particular, the database may include a particular degree of error or correction factor associated with different ranges of FFR values. The user may determine a degree of error for the calculated FFR of a current patient by first determining which range of FFR values the calculated FFR lies within, and then noting the degree of error associated with that particular range of FFR values. The degree of error associated with a range of FFR values at one part of the spectrum of empirically-collected FFR values may be less than the degree of error associated with a range of FFR values at another part of the spectrum. For example, in one embodiment, the degree of error associated with FFR values between 0.75 and 0.85 may be lower than the degree of error associated with FFR values in the upper range above 0.85-0.95 or in the lower range below 0.75. Still further, empirical data may suggest that FFR values in the upper range should be adjusted by downwardly by an offset factor X, while FFR values in the lower range should be adjusted upwardly by an offset factor Y. In one example, the offset factors X and Y are determined based on the empirically collected data and vary depending on how far the calculated FFR value is from the center range of 0.75-0.85. Thus, a calculated FFR value of 0.96 may be adjusted downwardly by a larger offset factor X than a calculated FFR value of 0.87. In still a further aspect, empirical data may suggest that errors in the calculation of FFR values are influenced by other inputs, such as vessel diameter, and the offset factors X and Y may be adjusted accordingly.

In another aspect, the database of FFR data and associated degrees of error may be used to train the algorithms for assessing FFR. In one aspect, the algorithm may utilize the calculated FFR (i.e., the range of FFR values in the database within which the calculated FFR lies) to determine a course of action for the patient. In one example, if the calculated FFR lies within the range of FFR values between 0.75 and 0.85, the algorithm to indicate the need for further diagnostic evaluation of the vessel. For example, in some embodiments, the FFR may indicate the need to obtain pressure-based flow measurements (e.g., by utilizing a pressure sensor mounted to a guidewire or catheter) to further evaluate or re-calculate the calculated FFR. In other instances, an FFR value in the upper range may direct the algorithm to indicate the need for treatment without further diagnostic evaluation of the vessel. Similarly, an FFR value in the lower range may indicate to the user that no treatment is currently necessary.

Figure 7:
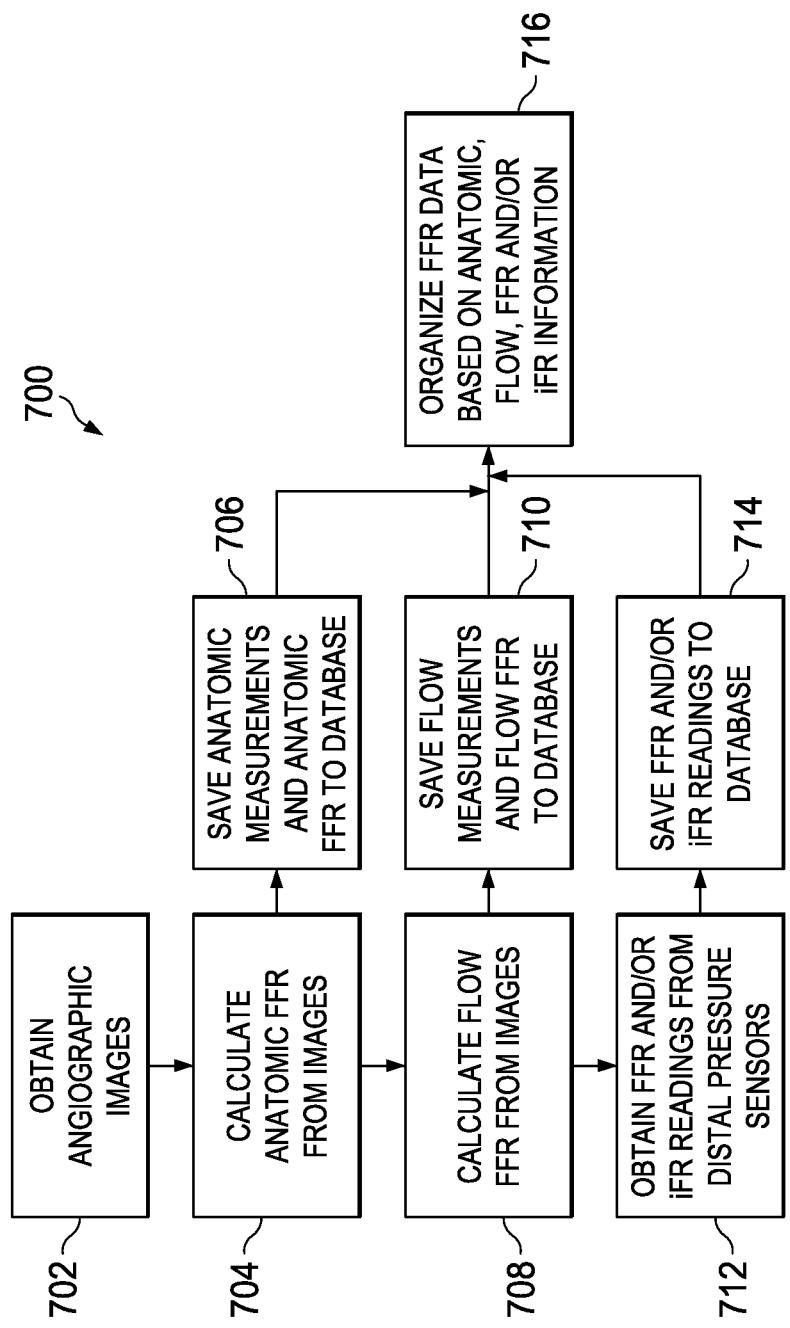
FIG. 7 is a flow chart showing various steps of obtaining FFR data and creating a database for subsequent correlation with subsequent patient measurements.

Referring now to FIG. 7, there is shown a methodology 700 of creating a database or look-up table having the correlated information for each patient of the anatomical FFR, the calculated flow FFR and the sensed pressure FFR and/or iFR information. Each patient within a record group will have their imaged and sensed data stored in the database to build a patient population of FFR data. At step 702, angiographic images are obtained. As explained above, measurements are taken from the images and a calculation of the anatomic FFR is made at step 704. The measurements, along with the sensed aortic pressure, and the calculated anatomic FFR values are saved to the patient database at step 706. The method can continue, although not required, to calculating the flow FFR at step 708 as described above. If additional images capturing contrast media flow are needed those can also be taken as this point. The flow measurements and flow FFR value are saved to the database at step 710. The method continues with obtaining distal pressure readings with a sensor mounted on a guidewire or catheter as described above. The pressure values are used to approximate the sensed FFR value if adenosine is used. If no hyperemic agent is used, the sensed values are used to determine an iFR value. These sensed pressure measurements along with the corresponding FFR and/or iFR values are saved in the database at step 714. As step 716, the database can be organized so the data can be queried based on any of the saved values. Although the method contemplates multiple forms of FFR related data, not all patients will have all types of FFR data. As the FFR database is populated with sensed data from multiple patients, queries may be run against the database information to determine best approximations for FFR for a vessel with the closest matching parameters based on less than all of the sensed data parameters.

In one aspect, a subsequent patient may have an angiographic procedure generating images. The images may be used to measure anatomic features and generate an anatomic FFR having a first weighted value. The anatomic features may also be used to query the database for database patients having similar anatomic features. The FFR values for database patients can then be used to more closely estimate the actual FFR value of the subsequent patient. Specifically, in one non-limiting example, if a series of ten database patients having similar anatomic feature measurements to the subsequent patient exist, the sensed FFR readings for the ten patients will be averaged and returned as the approximate anatomic FFR value.

In addition, the anatomic FFR value will receive a certainty rating from 1 to 10 with 10 being the highest indicating how close the database patient parameters match the subsequent patient parameters and how many matching entries are in the database. In addition or as an alternative, the estimated anatomic FFR score may be color coded as an indication of reliability. The same type of database comparison can also be made using the flow FFR and comparing that information to the database patient flow FFR data.

Figure 8:
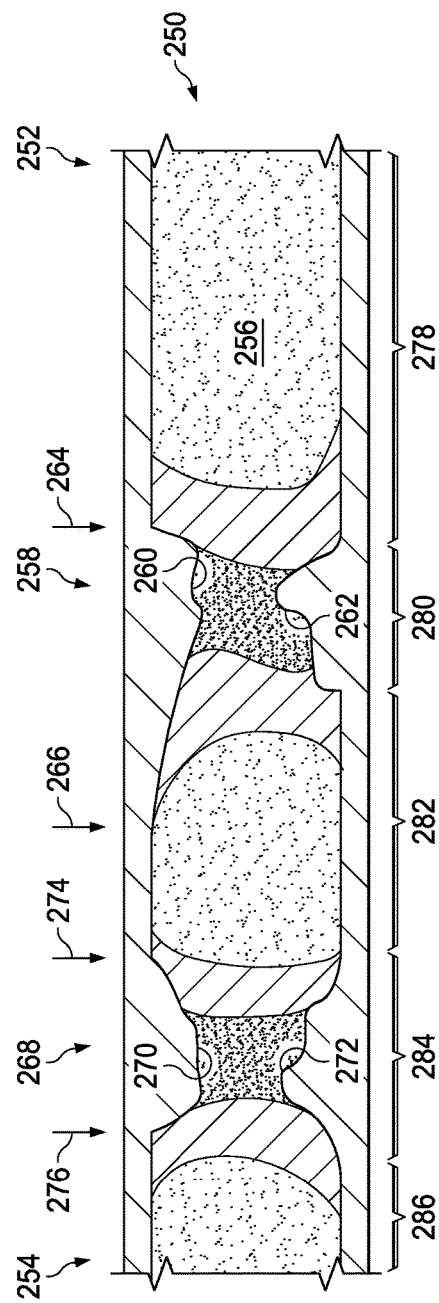
FIG. 8 illustrates a composite representation of the calculated FFR data.

Referring now to FIG. 8, there is shown a representation of an occluded vessel 250 similar to the vessel of FIG. 5. The sensed data and determined flow information is graphically represented on the vessel image to show the user areas of change in the flow of blood through the vessel. Specifically, darker shaded areas represent locations of lowest or restricted flow, and hatched areas represent areas of low flow while speckled areas represent regions of satisfactory flow. It will be appreciated that colors could be used to shade these areas such as a red for restricted flow, yellow for low flow and green for satisfactory flow.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of evaluating a vessel of a patient, comprising:

obtaining, via an angiography/fluoroscopy unit, a first set of angiographic images of the vessel having a lesion from a first view plane, the lesion having a lesion length extending from a proximal lesion end to a distal lesion end;

collecting, via a computing device in communication with the angiography/fluoroscopy unit, a first set of anatomic vessel measurements from the first set of angiographic images, the first set of anatomic vessel measurements including at least one first lesion diameter, a first proximal vessel diameter proximal to the lesion, and a first distal vessel diameter distal to the lesion;

determining, via the computing device, a first flow value utilizing the at least one first lesion diameter based on the first set of angiographic images;

creating, via the computing device, a hypothetical vessel representative of the vessel without the lesion, the hypothetical vessel comprising a hypothetical lumen extending uniformly from a proximal end with the first proximal vessel diameter to a distal end with the first distal vessel diameter, wherein the first proximal vessel diameter and the first distal vessel diameter are based on the first set of angiographic images;

determining, via the computing device, a second flow value for the hypothetical vessel; and calculating, via the computing device, a first anatomical fractional flow reserve for the vessel by dividing the first flow value by the second flow value.

2. The method of claim 1, wherein collecting the first set of anatomic measurements comprises collecting a plurality of first lesion diameters along the lesion length.

3. The method of claim 1, wherein collecting a first set of anatomic vessel measurements comprises collecting anatomic vessel measurements from the first set of angiographic images.

4. The method of claim 1, further comprising sensing a pressure proximal of a lesion within the vessel, the lesion having a lesion length extending from a proximal lesion end to a distal lesion end.

5. The method of claim 4, wherein sensing the pressure proximal of a lesion within the vessel comprises sensing an aortic pressure.

6. The method of claim 4, wherein determining the first flow value includes utilizing the sensed pressure.

7. The method of claim 4, wherein determining the second flow value includes utilizing the sensed pressure.

8. The method of claim 1, wherein obtaining a first set of angiographic images of the vessel comprises obtaining the angiographic images while a contrast agent of a first volume is flowing through the vessel.

9. The method of claim 8, wherein determining the first vessel flow value includes utilizing at least one characteristic of the flow of the contrast agent through the vessel.

10. The method of claim 8, wherein determining the second vessel flow value includes utilizing at least one characteristic of the flow of the contrast agent through the hypothetical vessel.

11. The method of claim 10, wherein utilizing the at least one characteristic comprises utilizing the amount of time elapsed for the first volume of the contrast agent to flow through the vessel.

12. The method of claim 10, wherein utilizing the at least one characteristic comprises utilizing visual changes reflecting the changing concentration of the contrast agent as it flows through the vessel.

13. The method of claim 12, wherein utilizing the visual changes comprises utilizing changes in pixilation of points of interest along the vessel.

14. The method of claim 12, wherein utilizing the visual changes comprises utilizing changes in color along the vessel.

15. The method of claim 1, wherein the hypothetical lumen comprises a generally uniform diameter extending between the proximal end and the distal end.

16. The method of claim 1, wherein the hypothetical lumen comprises a uniformly tapered diameter extending between the proximal end and the distal end.

17. The method of claim 1, wherein creating a hypothetical vessel comprises utilizing a border detection algorithm to identify a vessel wall boundary beneath the lesion.

18. The method of claim 1, wherein creating a hypothetical vessel comprises utilizing a point-to-point selection method to create a representation of the vessel extending from a first point of the vessel having the first proximal vessel diameter to a second point of the vessel having the first distal vessel diameter.

19. The method of claim 1, further comprising:

obtaining a second set of angiographic images of the vessel from a second view plane, the second view plane being different from the first view plane; and collecting a second set of anatomic vessel measurements from the second set of angiographic images, the second set of anatomic vessel measurements including a second lesion diameter, a second proximal vessel diameter proximal to the lesion, and a second distal vessel diameter distal to the lesion.

20. The method of claim 19, wherein determining the first flow value comprises utilizing the first set of anatomic measurements and the second set of anatomic measurements to calculate a first flow value.

21. The method of claim 19, wherein collecting the second set of anatomic measurements comprises collecting a plurality of second lesion diameters along the lesion length.

22. The method of claim 19, further comprising creating a three-dimensional representation of the vessel utilizing the first set of angiographic images and the second set of angiographic images.

23. The method of claim 22, wherein collecting a first set of anatomic vessel measurements comprises collecting anatomic vessel measurements from the three-dimensional representation of the vessel.

24. The method of claim 22, further comprising:

collecting a third set of anatomic vessel measurements from the three-dimensional representation of the vessel, the third set of anatomic vessel measurements including a third lesion diameter, a third proximal vessel diameter proximal to the lesion, and a third distal vessel diameter distal to the lesion; and determining a third flow value utilizing the at least one third lesion diameter and the sensed pressure.

25. The method of claim 24, further comprising calculating a second anatomical fractional flow reserve for the vessel by dividing the third flow value by the second flow value.

26. The method of claim 25, further comprising calculating a composite anatomical fractional flow reserve for the vessel by utilizing both the first anatomical fractional flow reserve for the vessel and the second anatomical fractional flow reserve for the vessel.

27. The method of claim 1, further comprising storing the first set of anatomic vessel measurements, the sensed pressure, and the first anatomic fractional flow reserve to a database as correlated data.

28. The method of claim 27, further comprising determining a degree of error for the first anatomical fractional flow reserve by utilizing the database of correlated data.

29. The method of claim 28, wherein determining the degree of error for the first anatomical fractional flow reserve comprises selecting the degree of error associated with a range of fractional flow reserve values within the database that contains the first anatomical fractional flow reserve.

30. The method of claim 1, wherein calculating the first anatomical fractional flow reserve comprises calculating an estimate of a fractional flow reserve calculated using pressure values.

* * * * *